US011951291B2

(12) United States Patent
Kourtis et al.

(10) Patent No.: US 11,951,291 B2
(45) Date of Patent: Apr. 9, 2024

(54) STATUS SENSING SYSTEM FOR INJECTION DEVICE

(71) Applicant: Eli Lilly and Company, Indianapolis, IN (US)

(72) Inventors: Lampros Kourtis, Cambridge, MA (US); Sean Matthew Pszenny, Cambridge, MA (US); Oliver Brian Regele, Cambridge, MA (US)

(73) Assignee: Eli Lilly and Company, Indianapolis, IN (US)

( * ) Notice: Subject to any disclaimer, the term of this patent is extended or adjusted under 35 U.S.C. 154(b) by 780 days.

(21) Appl. No.: 17/045,352

(22) PCT Filed: Apr. 12, 2019

(86) PCT No.: PCT/US2019/027125
§ 371 (c)(1),
(2) Date: Oct. 5, 2020

(87) PCT Pub. No.: WO2019/204133
PCT Pub. Date: Oct. 24, 2019

(65) Prior Publication Data
US 2021/0146052 A1  May 20, 2021

Related U.S. Application Data

(60) Provisional application No. 62/659,883, filed on Apr. 19, 2018.

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/3202* (2013.01);
(Continued)

(58) Field of Classification Search
CPC .............. A61M 5/3157; A61M 5/2033; A61M 5/3202; A61M 5/3234; A61M 2205/3317; A61M 2205/3576
See application file for complete search history.

(56) References Cited

U.S. PATENT DOCUMENTS 4,498,843 A  2/1985  Schneider et al.
7,018,363 B2  3/2006  Cowan et al.
(Continued)

FOREIGN PATENT DOCUMENTS

DE  19643813 A  4/1998
EP  3216472     9/2017
(Continued)

OTHER PUBLICATIONS

Office action issued by the Japan Patent Office dated Dec. 13, 2021 pertaining to Patent Application No. 2021-504142.
(Continued)

*Primary Examiner* — Dung T Ulsh
(74) *Attorney, Agent, or Firm* — Arthur C. H. Shum

(57) ABSTRACT

An injection device assembly including a housing, a syringe, a drive mechanism and a status sensing system and a module are described. The drive mechanism advances the syringe from a storage position to an injection position, and a plunger advances the syringe piston from an initial position to a final position. The status sensing system includes a light emitter that emits electromagnetic radiation into the housing transverse to the longitudinal axis, a light detector and a controller. The system determines a current status condition from at least three of the following five status conditions: 1) an injection ready state; 2) a needle insertion state; 3) a drug delivered state; 4) a needle guard present state; and 5) a needle retraction state.

21 Claims, 11 Drawing Sheets

(52) U.S. Cl.
CPC ... *A61M 5/3234* (2013.01); *A61M 2205/3317* (2013.01); *A61M 2205/3576* (2013.01)

(56) References Cited

U.S. PATENT DOCUMENTS

| | | | |
|---|---|---|---|
| 2005/0161467 | A1 | 7/2005 | Jones |
| 2012/0268741 | A1 | 10/2012 | Pommereau et al. |
| 2015/0085286 | A1 | 3/2015 | Whalley et al. |
| 2017/0246399 | A1 | 8/2017 | Forlani et al. |
| 2018/0064881 | A1* | 3/2018 | Whalley ............... G01F 11/025 |
| 2018/0161505 | A1* | 6/2018 | Prager ...................... A61M 5/24 |
| 2019/0083708 | A1* | 3/2019 | Säll ...................... A61M 5/3157 |
| 2019/0192778 | A1* | 6/2019 | Rehbein .............. A61M 5/3155 |
| 2019/0201627 | A1* | 7/2019 | Helmer ............... A61M 5/2033 |

FOREIGN PATENT DOCUMENTS

| | | |
|---|---|---|
| JP | 2017524399 | 8/2017 |
| WO | 1994008208 | 4/1994 |
| WO | 2002056934 | 7/2002 |
| WO | 2004009163 | 1/2004 |
| WO | 2011032960 | 3/2011 |
| WO | 2014090252 | 6/2014 |
| WO | 2015136564 | 9/2015 |
| WO | 2015187793 | 12/2015 |
| WO | 2016023846 | 2/2016 |
| WO | 2016036574 | 3/2016 |
| WO | 2017009724 | 1/2017 |
| WO | 2018013843 | 1/2018 |
| WO | 2018041798 | 3/2018 |
| WO | 2018046680 | 3/2018 |

OTHER PUBLICATIONS

Patent Cooperation Treaty International Search Report pertaining to International Application No. PCT/US2019/027125; International filing date: Apr. 12, 2019; dated Jul. 15, 2019.
Patent Cooperation Treaty Written Opinion of the International Searching Authority pertaining to International Application No. PCT/US2019/027125; International filing date: Apr. 12, 2019; dated Jul. 15, 2019.

* cited by examiner

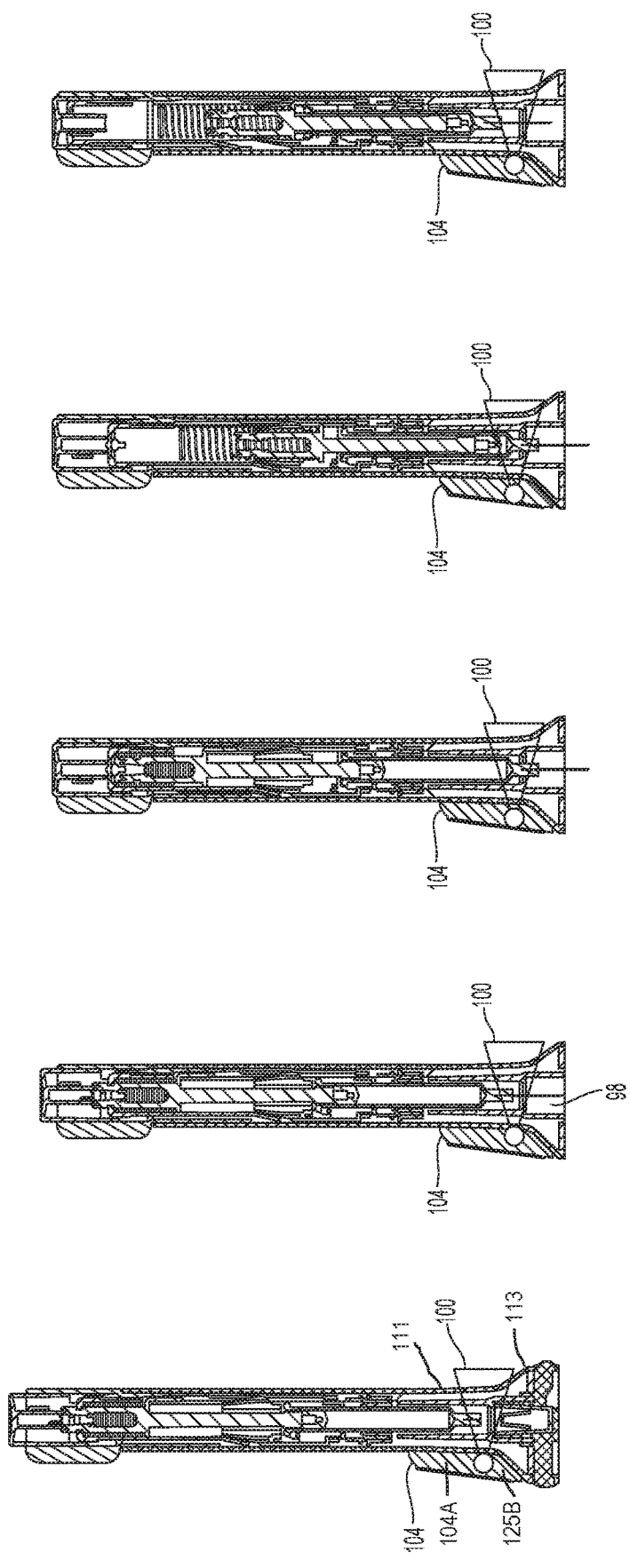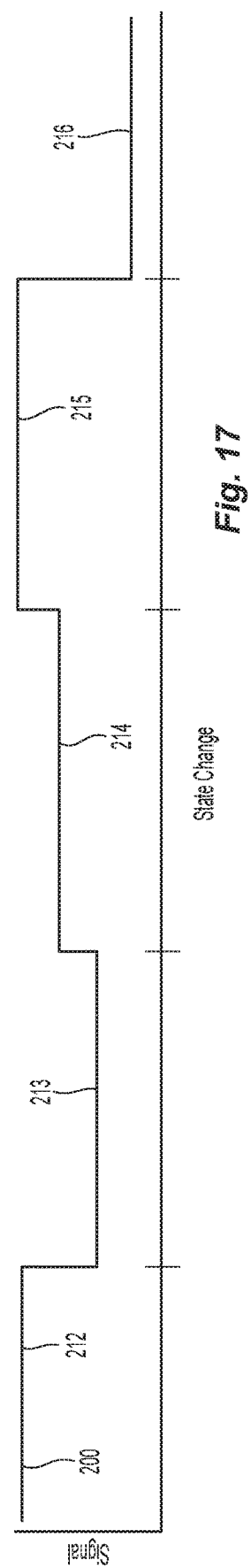

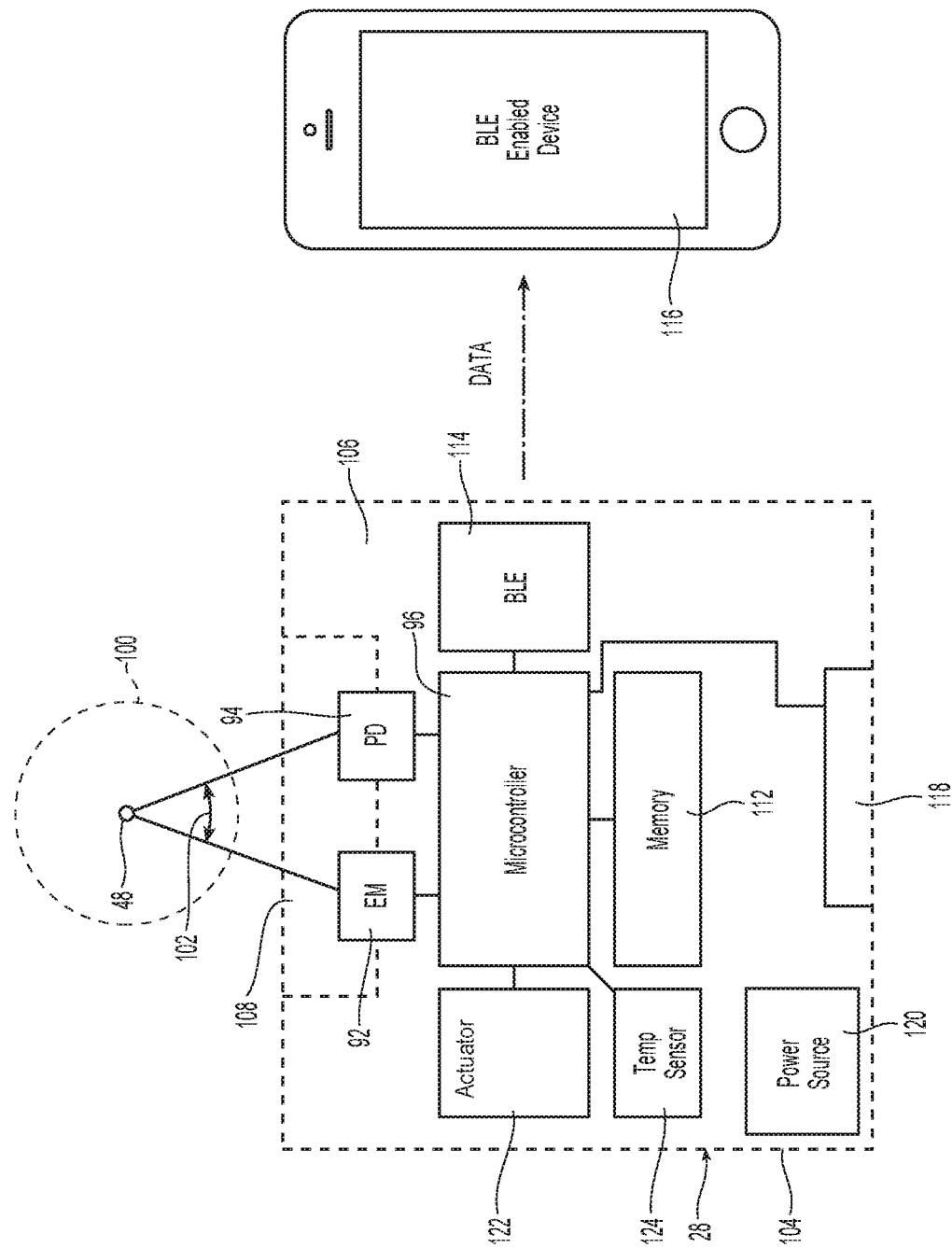

STATUS SENSING SYSTEM FOR INJECTION DEVICE

BACKGROUND

The present disclosure relates to medication delivery devices, and in particular, to status sensing systems used in medication delivery devices.

Injection devices in the form of a syringe or which include a syringe are widely employed by medical professionals and patients who self-medicate. Patients suffering from a number of different diseases frequently must inject themselves with medication and a variety of devices have been developed to facilitate such self-medication. In one example, the use of an automatic injection device which includes mechanisms to perform some of the steps of the injection process renders it more convenient for a patient to self-medicate particularly by patients with limited manual dexterity. Automatic injection devices are typically a single use device that is disposed after use. Therefore, adding electronics or multiple sensing units within the device may be cost prohibited and less environmentally friendly.

SUMMARY

In one form, an injection device assembly includes an injection device and a status sensing system. The status sensing system includes a light emitter configured to emit electromagnetic radiation in a direction transverse to the longitudinal axis and into the interior volume, a light detector configured to detect electromagnetic radiation emitted from the light emitter and configured to generate a signal responsive to the detected electromagnetic radiation, and a controller in electrical communication with the light emitter and the light detector. The controller is configured to determine the status of said device based at least in part upon the generated signal. The controller is configured to determine a current status condition between at least three status conditions of said device including: i) an injection ready state wherein the syringe assembly is in the storage position and the piston is in the initial piston distal position; ii) a needle insertion state wherein the syringe assembly is in the injection position and the piston is in the initial piston distal position; and iii) a drug delivered state wherein the syringe assembly is in the injection position and the piston is in the final piston proximal position.

In another form, a method of determining a current status condition of an injection device is provided. The steps include determining an injection ready state wherein the syringe assembly is in the storage position and the piston is in the initial piston distal position. The steps include determining a needle insertion state wherein the syringe assembly is in the injection position and the piston is in the initial piston distal position. The step includes determining a drug delivered state wherein the syringe assembly is in the injection position and the piston is in the final piston proximal position.

In another form, a sensor module for removable attachment to an injection device is provided. The sensor module includes a sensor module housing and a status sensing system coupled to the sensor module housing. The status sensing system includes a light emitter configured to emit electromagnetic radiation in a direction transverse to a longitudinal axis of said injection device, a light detector configured to detect electromagnetic radiation emitted from the light emitter and configured to generate a signal responsive to the detected electromagnetic radiation, and a controller in electrical communication with the light emitter and the light detector, the controller configured to determine a current status of said injection device based at least in part upon the generated signal.

BRIEF DESCRIPTION OF THE DRAWINGS

The above mentioned and other features of this present disclosure, and the manner of attaining them, will become more apparent and the invention itself will be better understood by reference to the following description of an embodiment of the present disclosure taken in conjunction with the accompanying drawings, wherein:

FIG. 12 is a cross sectional view of the injection device and the status system module taken along line A-A of FIG. 11.

FIG. 13 is a cross sectional view of the injection device and the status system module taken along line A-A of FIG. 11, with the end cap and needle guard removed.

FIG. 14 is a cross sectional view of the injection device and the status system module taken along line A-A of FIG. 11, with the injection needle advanced to inject a patient.

FIG. 15 is a cross sectional view of the injection device and the status system module taken along line A-A of FIG. 11, after completing the discharge of the medication from the syringe assembly.

FIG. 16 is a cross sectional view of the injection device and the status system module taken along line A-A of FIG. 11, after retracting the needle following an injection event.

FIG. 17 is a chart showing the signal generated by light detector of the status sensing system over the course of an injection event.

FIG. 18 is a schematic representation of the status sensing system of the module and an external device.

Figure 1:
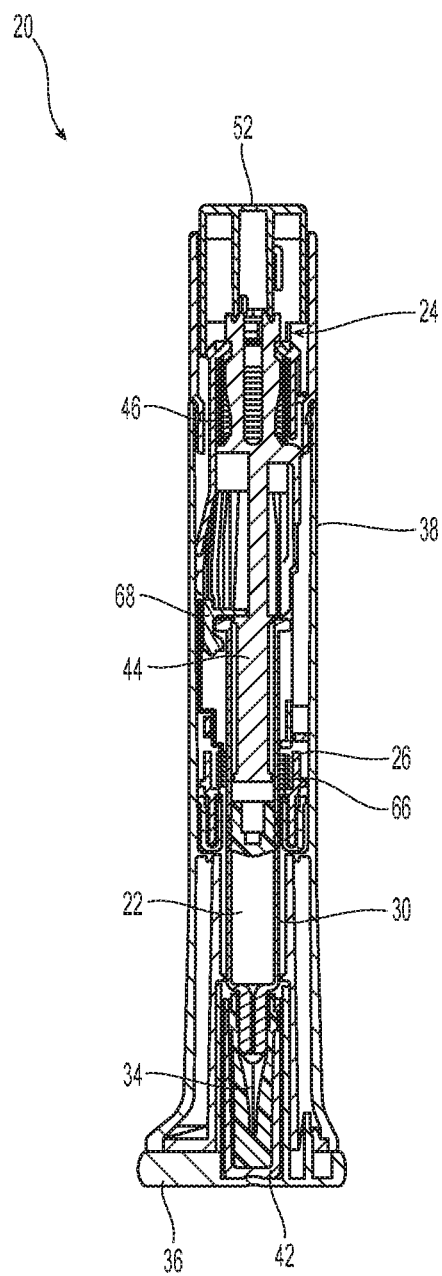
FIG. 1 is a cross sectional view of an injection device prior to use.

Corresponding reference characters indicate corresponding parts throughout the several views. Although the exemplification set out herein illustrates embodiments of the present disclosure, in several forms, the embodiments disclosed below are not intended to be exhaustive or to be construed as limiting the scope of the invention to the precise forms disclosed.

DETAILED DESCRIPTION

The present disclosure relates to sensing systems for medication delivery devices. Sensing system may be incorporated into a removable module that attaches to the delivery device or one that may be integrated within the deliver device. The sensing system can determine the current operational status of the device during its operational use based on the sensing of the location of device components that enter and exit a detection zone targeted by the sensing system. The may be beneficial for single use devices where dose delivery detection is too expensive to include since a single use device will have a fixed amount of dosage which can be automatically or manually inputted into an external device. There may be benefit to only knowing that the drug was used for treatment, rather than knowing or logging the exact amount delivered. Signals representative of the sensed position of relative device components are correlated to one of many different states of the device. The current status can be continuously indicated via, for example, a display or LEDS, or otherwise communicated to the user of the device to facilitate correct and convenient use of the device. When the user is informed of the operational status of the device as it is being used, the user is less likely to take an action, such as removing the device from the injection site before completion of the drug delivery, which might compromise the effective use of the device. By way of illustration, the medication delivery device is described in the form of an auto-injector device. However, the medication delivery device may be any device which is used to deliver a dose of a medication, such as pen injectors, infusion pumps and syringes. The medication may be any of a type that may be delivered by such a medication delivery device. It may be advantageous to provide a single sensing system positioned along the device to capture at least one of a needle guard present state, an injection ready state, a needle insertion state, a drug delivered state, and a needle retraction state, or any combination thereof. It may be beneficial to determine whether the dose was delivered and/or the operational states during the injection process with a module without having to change the mechanical architecture of the drive mechanism of the delivery device.

Figure 2:
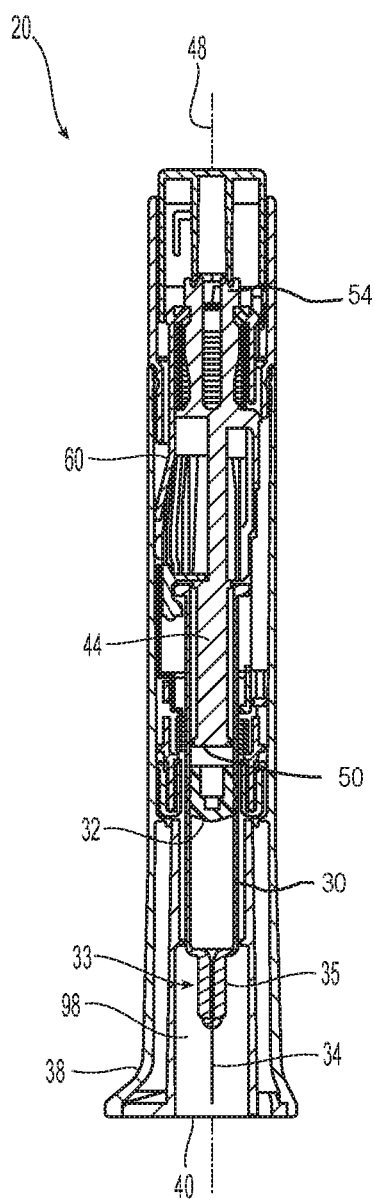
FIG. 2 is a cross sectional view of the injection device with the syringe assembly in a storage position and ready for an injection event.
Figure 3:
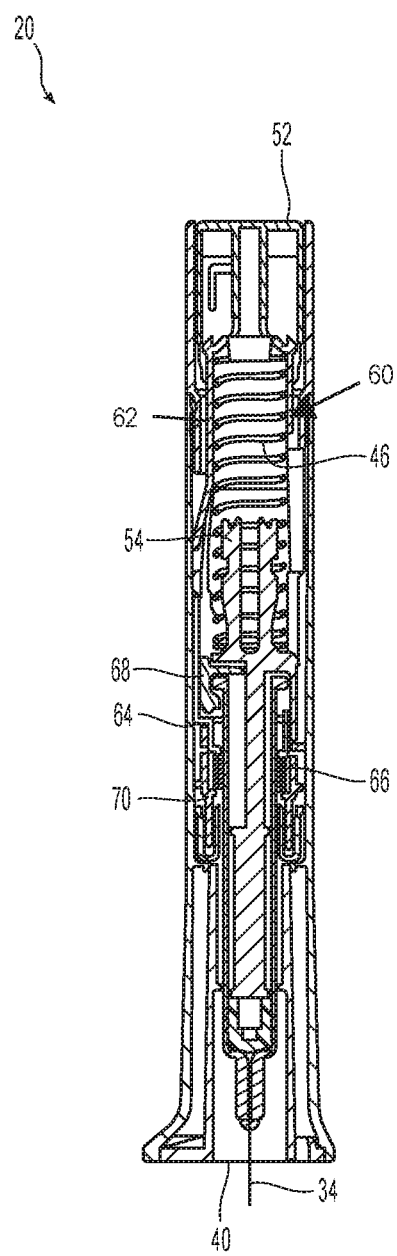
FIG. 3 is a cross sectional view of the injection device with the syringe assembly in an injection position.
Figure 4:
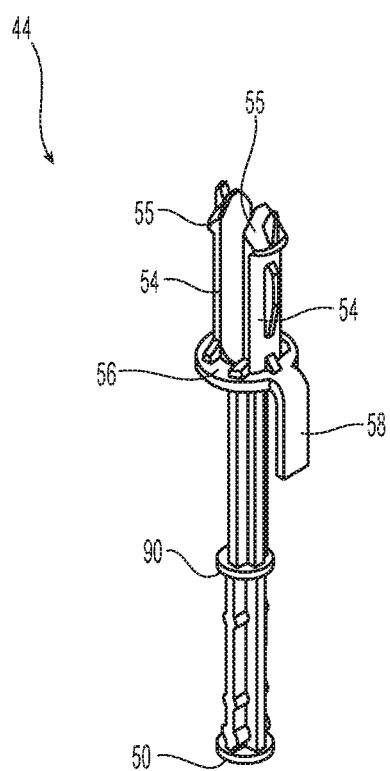
FIG. 4 is a perspective view of a plunger.
Figure 9:
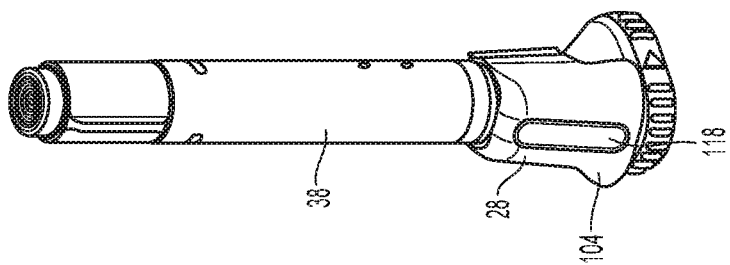
FIG. 9 is a perspective view of the injection device and the status sensing system module of FIG. 8 attached together.

In FIGS. 1-3, a medication injection device 20 is depicted in various operational states. One example of such a device and its operation is described in U.S. Pat. No. 8,734,394 B2 issued May 27, 2014 to Adams et al., the disclosure of which is hereby incorporated herein by reference. Device 20 includes a syringe assembly 22, a drive mechanism 24, and a retraction mechanism 26, and may include a status sensing system 28 shown later in a module, for example, in FIG. 9, attachable to the injection device 20. Syringe assembly 22 includes a barrel 30 forming a container body for holding a medication, and a piston 32 disposed within the barrel 30 for driving the medication outside the barrel. Syringe assembly 22 also includes a needle assembly 33 having a hollow injection needle 34 and a needle hub 35 which mounts needle 34 to syringe barrel 30. Advancing piston 32 within barrel 30 toward needle 34 dispenses medication through needle 34.

Devices described herein, such as device 20, may further comprise a medication, such as for example, within the syringe barrel 30. In another embodiment, a system may comprise one or more devices including device 20 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

FIG. 1 illustrates device 20 in its initial, pre-use configuration. Here, an end cap 36 is secured to an injection device housing 38 and covers a proximal end opening 40 in housing 38. Housing 38 may be formed from a plastic material and is shown extending generally longitudinally between a distal end in close proximity to an actuating button 52 and a proximal end in close proximity to the proximal end opening 40 along a longitudinal axis 48. A needle guard 42 is mounted on syringe assembly 22 and covers and surrounds needle 34. End cap 36 and needle guard 42 protect the user from accidental needle pricks and also protect needle 34 from damage. When using device 20 to dispense medication, for example, injecting the medication into a patient, end cap 36 and needle guard 42 are first removed. FIG. 2 illustrates device 20 after removal of end cap 36 and needle guard 42 from syringe assembly 22 that is in a storage position and device 20 ready for a dispensing event.

Syringe assembly 22 is moveable relative to the injection device 20 between a storage position and an injection position. FIG. 3 illustrates device 20 after the syringe assembly 22 has been moved relative to device 20 to an injection position from its storage position that is shown in FIG. 2. In the storage position (FIGS. 1 and 2), needle 34 is retracted to a position such that needle 34 is disposed within housing 38 of device 20. In the injection position (FIG. 3), needle 34 projects outwardly from housing 38 beyond proximal opening 40 in the proximal direction parallel to longitudinal axis 48 whereby needle 34 may be inserted into a patient.

Drive mechanism 24 includes a plunger 44 which engages piston 32. Drive mechanism 24 includes a spring 46 that drives plunger 44 in a translational movement. In the illustrated embodiment, spring 46 advances plunger 44 along a linear path defined by the longitudinal axis 48 of device 20. As plunger 44 is advanced, foot 50 of plunger 44 contacts piston 32. As the plunger 44 is further advanced, syringe assembly 22 is advanced along axis 48 from its storage position to its injection position. After advancement of syringe assembly 22 to its injection position, the continued proximal advancement of plunger 44 advances piston 32 proximally within barrel 30 from its initial piston position (shown in FIGS. 1 and 2) to its final piston position (shown FIG. 3) to cause medication to be dispensed from needle 34 in a dispensing event. Prior to any dispensing of medication and when syringe barrel 30 holds the full original volume of medication, piston 32 will be in its initial piston position. After advancing piston 32 the full extent of its travel length toward needle assembly 33, piston 32 will be in its final piston position proximate needle assembly 33 and the medication from within barrel 30 will have been discharged. In a single use, syringe assembly 22 will hold a single dose of medication which will be delivered in a single injection event and piston 32 will be advanced from its initial piston position to its final piston position in that single injection event to thereby delivery the entire single dose contents of syringe assembly 22. While the device is shown as a single use device, multiple-use devices may also benefit from status indication of the device during a single use.

The advancement of plunger 44 will generally not result in the dispensing of medication from syringe assembly 22 until after syringe assembly 22 has been advanced to the injection position. There are factors that can inhibit the medication from being dispensed before the syringe is advanced to the injection position. A factor can be the friction between piston 32 and barrel 30. Typically, piston 32 will be formed out of a rubber material and barrel 30 will be glass. The frictional resistance between these two components can be sufficient to prevent the advancement of piston 32 within barrel 30 until syringe assembly 22 is advanced to its injection position and engagement with a suitable stop member prevents the further advancement of syringe assembly 22. Additionally, the medication within the syringe may be somewhat viscous and thereby somewhat resistant to flowing out of needle 34. If necessary, modification of piston 32 and syringe barrel 30 to alter the frictional resistance of dispensing motion of the engagement member 32 relative to syringe barrel 30 can limit or prevent the premature dispensing of medication before container 22 reaches its injection position.

To activate drive mechanism 24, a person depresses actuating button 52 at the distal end of device 20. Depressing button 52 disengages one or two elongate prongs 54 on plunger 44 from a shuttle assembly 60 thereby allowing spring 46 to axially advance plunger 44. Spring 46 has a helical shape and surrounds prongs 54. The proximal end of spring 46 biasingly engages flange 56 on plunger 44.

Figure 6:
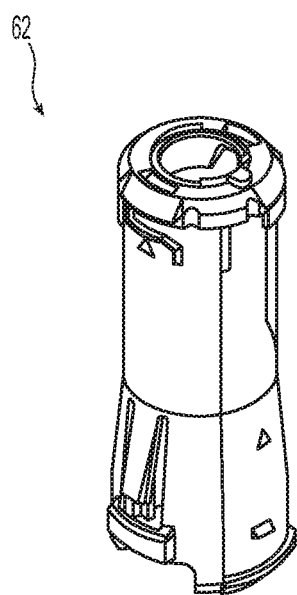
FIG. 6 is a perspective view of an upper shuttle member.
Figure 7:
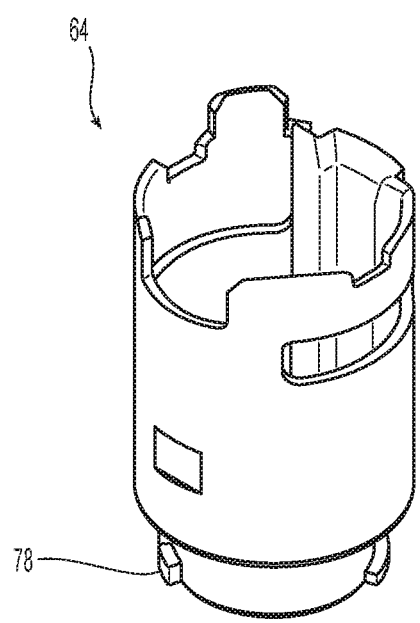
FIG. 7 is a perspective view of a lower shuttle member.
Figure 11:
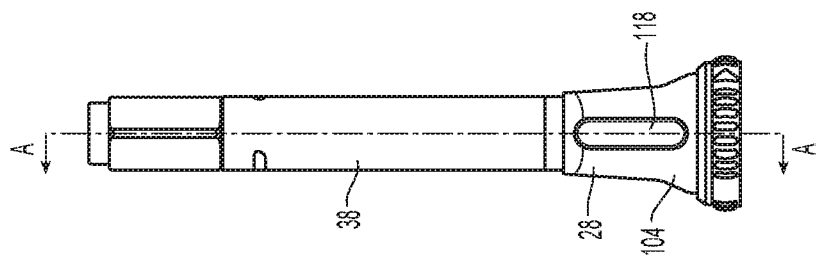
FIG. 11 is a front view of the injection device and the status sensing system module of FIG. 9.
Figure 10:
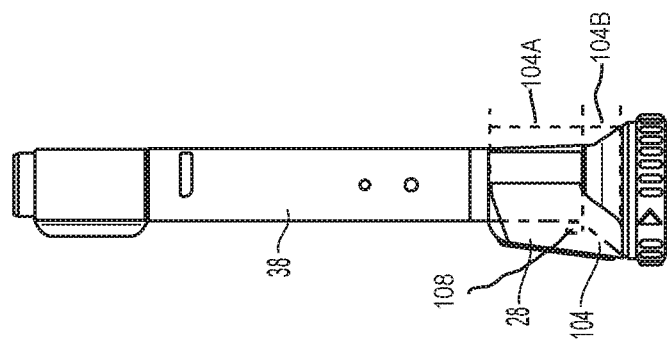
FIG. 10 is a side view of the injection device and the status sensing system module of FIG. 9.

Shuttle assembly 60 can include an upper shuttle member 62 shown in FIG. 6 and a lower shuttle member 64 shown in FIG. 7. Shuttle members 62, 64 are fixed together in the final assembly. In the final assembly, upper shuttle member 62 captures button 52 and spring 46 limiting the axial movement of these parts in the distal direction. Prongs 54 engage surfaces on upper shuttle 62 when the device is in the condition shown in FIGS. 1 and 2. Depressing button 52 causes tabs on button 52 to engage ramps 55 on prongs 54 to bias prongs 54 inwardly to disengage prongs 54 from upper shuttle member 62. After prongs 54 have been disengaged, spring 46 exerts a biasing force on flange 56 to advance plunger 44 from the position shown in FIG. 2 to the position shown in FIG. 3. As plunger 44 is advanced, it moves syringe assembly 22 to the injection position and then advances piston 32 to dispense medication as discussed above.

After the dispensing event is complete, retraction mechanism 26 moves syringe assembly 22 from the injection position shown in FIG. 3 back to the storage position. More specifically, the retraction mechanism is adapted to move the medication container from the injection position to the storage position in a retraction movement. In the illustrated embodiment, the retraction mechanism includes a spring 66, a syringe carrier 68 shown in FIG. 5 and a rotary member 70 that acts as a follower.

Plunger 44 can include an outrigger 58 which unlocks rotary member 70 as plunger 44 nears the end of its travel in the proximal direction. Rotary member 70 is rotationally secured to lower shuttle member 64 by engagement between a latch and a latching recess in lower shuttle member 64. Outrigger 58 unlocks member 70 by depressing the latch. Spring 66 is torsionally preloaded and has one end engaged with member 70 and an opposite end engaged with shuttle assembly 60. Upon depression of the latch, spring 66 causes member 70 to rotate. Member 70 can include a slot that receives a tab 78 on lower shuttle member 64. At one end of the slot, member 70 defines an axially extending channel. As member 70 is rotated, tab 78 can move within the slot on member 70 until tab 78 reaches the axially extending channel.

Member 70 is rotatable within housing 38 but is not axially moveable relative to housing 38. Other embodiments may include a member 70 is also axially movable. A radial flange on rotary member 70 can engage a ledge within housing member 38 to limit the proximal movement of member 70. Spring 66 can exert an axial force, torsional force, or both forces on member 70 to bias member 70 proximally to thereby maintain member 70 in an axial position where the radial flange of member 70 engages the interior ledge of housing member 38. Shuttle assembly 60 can include axially extending channels or ribs that engage corresponding features on housing member 38 that allow shuttle assembly 60 to move axially within housing 38 but which prevent the relative rotation of shuttle assembly 60 relative to housing member 38.

Spring 66 is also axially preloaded and exerts a distally directed biasing force on shuttle assembly 60. When tab 78 reaches the axially extending channel, spring 66 moves shuttle assembly 60 distally within housing 38 as tab 78 slides axially through the channel. A damping compound may be arranged adjacent rotary member 70 to slow the rotation of member 70 and allow for the completion of the dispensing event before tab 78 reaches the axially extending channel. For example, rotary member 70 may include a skirt with a plurality of axially extending tabs that are disposed in a grease collar to provide damping.

As shuttle assembly 60 moves distally, it carries syringe assembly 22 distally and moves it back to the storage position shown in FIG. 2. Spring 66 biases the retraction mechanism 26 distally and thereby maintains syringe assembly 22 in its storage position after an injection event. A locking mechanism such as a detent on the shuttle assembly 60 and a recess on the housing 38 member may additionally provide a locking engagement to secure syringe assembly 22 in the storage position with needle 34 disposed within housing 38 after an injection event whereby the user can then dispose or otherwise handle device 20 in a safe manner.

Figure 5:
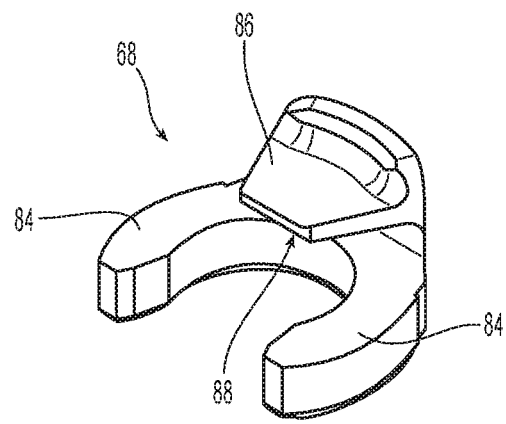
FIG. 5 is a perspective view of a syringe carrier.

Syringe carrier 68 is shown in FIG. 5. Arcuate arms 84 of carrier can grip barrel 30 of syringe assembly 22. Syringe carrier 68 also includes a flange 86. A flange on the syringe barrel 30 is captured between arms 84 and flange 86. A portion of the underside 88 of flange 86 engages small flange 90 on plunger 44 and thereby prevents proximal axial movement of syringe assembly 22 before plunger 44 is advanced. When shuttle 60 is being retracted, lower shuttle member 64 engages arms 84 to carry syringe assembly 22 distally back to its storage position.

In one embodiment, status sensing system 28 is provided within a sensor module housing 104 that is removably attached to the device 20. In this manner, the module housing 104 may be removed from a device after its use and disposal and reattached to another device. Status sensing system 28 may be beneficial for communicating to the user and/or health care provider that an injection occurred and the date/time of such injection. Other information may also be communicated such as the type of device, the type of medication, the amount and/or strength of medication. The illustrated module is shown as a side mounted or over the end mounted type of device. The module may comprise a cap configured for attachment to a needle end of a pen device.

In one embodiment, with additional reference to FIG. 18, status sensing system 28 includes a light emitter 92, a light detector 94 and a controller 96. The light emitter 92 is configured to emit electromagnetic radiation, continuously or by pulsing within a period of time, toward the device housing. In one example, the light emitter 92 can be a light emitting diode. In another example, the light emitter 92 can emit infrared radiation which can be influenced less by outside interference than LEDs, and in yet another example, the light emitter 92 can emit microwave radiation. The light emitter 92 may be more effective with the provision of windows to the interior of the device, or the light emitter may produce electromagnetic radiation capable of penetrating through the device housing with windows omitted. The light detector 94 is configured to detect the electromagnetic radiation emitted from the light emitter 92, and, particularly, positioned to detect the emitted portions of radiation from the light emitter 92 that have been reflected, refracted, or otherwise transmitted to the device housing. In one example, the light detector is a photodetector. The pair of light emitter 92 and light detector 94 can be selected for optical operation.

Light emitter 92 can be positioned to emit light in a direction transverse to longitudinal axis 48 and into the interior volume 98 of housing 38. Light detector 94 is positioned to detect light emitted from light emitter 92 and configured to generate a signal responsive to the detected light. The generated signal segment over time is different for each operational state depending on the relative positions of the moving components within the device housing. Controller 96 is in electrical communication with light emitter 92 and light detector 94 and is configured to determine the operational status of injection device 20 based at least in part upon the generated signal responsive to the detected light generated by light detector 94.

In the illustrated embodiment, the co-operation and targeted positioning of light emitter 92 and light detector 94 defines a detection zone 100, which can be three-dimensional, within interior volume 98 of housing 38. The detection zone 100 can be proximate to or at proximal opening 40 where light emitter 92 is positioned to emit light into detection zone 100 and light detector 94 is positioned to detect light from detection zone 100. In one example, the detection zone 100 initially does not include the piston or plunger, that is, these components are located distal to the detection zone. As explained in greater detail below, as different components of the injection device 20 enter and leave detection zone 100, the light leaving the detection zone and detected by light detector 94 will change thereby allowing controller 96 to differentiate between different status conditions of injection device 20. When the syringe assembly is in the storage position, the piston is disposed outside the detection zone. When the syringe assembly is in the injection position, piston 32 at its initial piston distal position is disposed outside the detection zone, and piston 32 at its final piston proximal position is disposed within the detection zone. The light detector is positioned to detect light that has been emitted from the light emitter and reflected, refracted, or otherwise transmitted toward the light detector from a point located within the detection zone.

In the illustrated embodiment, light detector 94 is positioned to detect light that has been emitted from light emitter 92 and reflected toward light detector 94 from a point located within detection zone 100. In other words, light detector 94 is positioned to detect light deflected by components of device 20 that are positioned in detection zone 100. As can be seen in the schematic depiction of system 28 provided within the module housing 104 in FIG. 18, light emitter 92 and light detector 94 define an angle 102 with respect to longitudinal axis 48. By positioning light emitter 92 and light detector 94 such that they have separation at the angle 102 relative to longitudinal axis 48 of less than 90 degrees, light detector 94 will detect primarily reflected light from light emitter 92. In the illustrated embodiment, light emitter 92 and light detector 94 are positioned to define a significantly smaller angle 102 of separation of approximately 20 degrees or less. Due to physical constraints, if light emitter 92 and light detector 94 are positioned in the same axial plane, there will necessarily be some angular distance between the two. Although optical lenses or reflectors could be used to effectively eliminate such angular separation, such additional expenses will generally be unnecessary.

Alternatively, light detector 94 could be positioned so that it detects light transmitted from light emitter 92 through detection zone 100 to light detector 94 without deflection. For example, light detector 94 could be positioned directly opposite light emitter 92 with detection zone 100 between light detector 94 and light emitter 92, i.e., with light detector 94 and light emitter 92 defining angular separation of 180 degrees relative to axis 48.

It is also noted that while the illustrated embodiment uses a single light emitter 92 and a single light detector 94, a plurality of light emitters 92 and/or a plurality of light detectors 94 can be used instead.

The status sensing system module 28 may be integrated into injection device housing 38 or, as in the illustrated embodiments, it may be housed within the module housing 104 that removably attachable to injection device housing 38.

In the illustrated embodiment, status sensing system 28 may be included within the exterior module housing 104. Module housing 104 defines an interior space 106. Light emitter 92, light detector 94 and controller 96 are disposed within interior space 106. Module housing 104 also defines a sensor opening 108 in communication with interior space 106 where light emitter 92 is positioned to emit light outwardly through the sensor opening 108 and light detector 94 is positioned to detect light entering interior space 106 through sensor opening 108.

Figure 8:
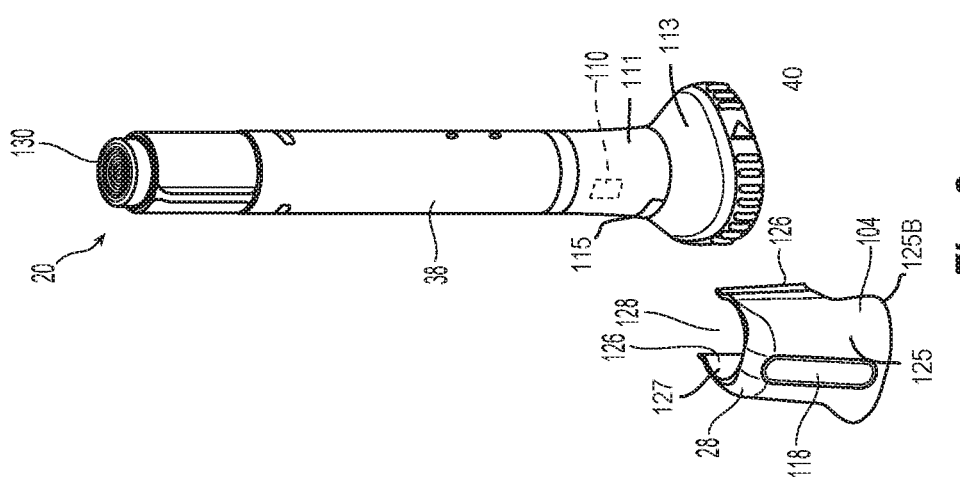
FIG. 8 is a perspective view of the injection device and an unattached status sensing system module.

As shown in FIG. 8, injection device housing 38 defines a window portion 110 that allows the transmission of light emitted by light emitter 92 into the interior volume 98 of injection device housing 38 proximate opening 40 and allows the transmission of light from interior volume 98 to light detector 94 when module housing 104 is attached to injection device housing 38. Window portion 110 may be made of a transparent or translucent material. In one embodiment, the cylindrical segment 111 of the device housing 38, for example, a 10% segment, may define the window portion 110, while in other embodiments, the size of the segment that defines the window portion may be at least 50% and up to 100%. In some devices, a window is omitted as the light emitter and light detector are configured to transmit through the wall of the housing, rather than through a window.

When system module 28 is integrated with housing 38, light emitter 92 and light detector 94 can be positioned within interior volume 98 of injection device housing 38 to thereby avoid having a window portion, or, the light emitter 92 and light detector 94 could be permanently mounted on an exterior portion of injection device housing 38 and communicate with interior volume 98 through a window portion.

Module housing 104 and injection device housing 38 are cooperatively configured such that window portion 110 is in communication with sensor opening 108 when the illustrated status sensing system 28 is attached to the device housing 38 so that window portion 110 allows the transmission of light emitted by the light emitter 92 into interior volume 98 and allows the transmission of light from interior volume 98 to light detector 94.

Placing window portion 110 in communication with sensor opening 108 allows the passage of light but does not imply that there are no partitions between the interior volume of injection device housing 38 and the interior space 106 of module housing 104. While window portion 110 could be formed by one or more openings in injection device housing 38, window portion could alternatively be formed out of a solid material that is substantially transparent to the light emitted by light emitter 92 and detected by light detector 94 at locations proximate the positons of light emitter 92 and light detector 94. In the illustrated embodiment, the entire portion of the injection device housing 38 located near proximal opening 40 and surrounding interior volume 98 can be formed out of a clear polymeric material which is transparent to the light wavelength emitted and detected by status sensing system 28 and thereby forms the window portion 110. In another example, the window is omitted and the light emitter and light detector co-operatively permit electromagnetic radiation, such as, for example, through infrared or microwave radiation, that penetrates through the wall of the device housing.

One example of the sensing system 28 is depicted in FIG. 18. With additional reference to FIG. 8, the module housing 104 may include an optional electronic display 118. Although not shown, display 118 is circuited to and controlled by an electronic controller 96 or controller assembly mounted within module housing 104. Controller 96 may include conventional components such as, for example, a processor, power source 120, memory 112, etc. Controller 96 is programmed to achieve the electronic features of device 20, including driver software for causing the display of information on the display 118. The information displayed in display 118 is determined by controller 96 via information from the sensing system 28, which is electrically circuited with controller 96. The controller 96 includes control logic operative to perform the operations described herein, including detecting and/or communicating a current operational status of medication delivery device 20. Operational status may include a particular step, a time, a date, a duration, a kind of device, a kind of drug, a strength or dosage of drug, a user identification.

The controller 96 is operable to determine the operational status based on signals generated by the system 28. The status can be determined by associating the electrical characteristic (such as voltage or resistance) to a predefined signal value stored into database, look up table, or other data stored in memory 112. The controller 96 may be operative to store the detected status in local memory 112 (e.g., internal flash memory or on-board EEPROM). The controller 96 may be further operative to wirelessly transmit via a wireless communication module 114 a signal representative of the detected status to a paired remote electronic device, such as a user's smartphone, over a Bluetooth low energy (BLE), near-field communication (NFC) or other suitable short or long-range wireless communication protocol. Illustratively, the BLE control logic and controller are integrated on a same circuit.

The status sensing system 28 may optionally include various other components. For example, the memory 112 of status sensing system 28 is schematically depicted in FIG. 18 as a digital memory which can be used to record the time, date and other data related to each of the injection events monitored by status sensing system 28. In this regard, it is noted that by employing the status sensing system 28 within the module housing 104 that can be removably attached to injection device 20, the module housing 104 can be detached by the user from a used injection device 20 and attached to a new injection device 20 for the next injection event. Status sensing system 28 can store a data record of multiple injection events in memory 112 that each employ a separate, disposable single dose injection device 20. Such data can provide valuable information such as confirming that patients are properly completing their medication injections and at the correct time intervals. Analysis of such data may also provide valuable insights into the patient's adherence to the proscribed medication regime and could be combined with other data concerning patient behavior and activities to provide still more valuable insights into managing the health of the patient.

The illustrated communication module 114 includes a wireless communication capability such as a transceiver employing Bluetooth low energy communication protocols. Module 114 is in communication with controller 96 and controller 96 includes control logic operative to communicate with an external device 116, such as the illustrated smart phone or other external electronic device, such as servers, computers, or other computing systems, capable of receiving wireless Bluetooth communication to thereby transmit data from status sensing system 28. Other communication protocols may alternatively be employed, or, including the module having a connector port, such as, for example, a USB or firewire interface, for operable use with a wired link to communicate data to an external device.

Such communication may be done periodically to transfer stored data from memory 112 to external device 116 or it may be used to communicate data from status sensing system 28 in real time. For example, if device 116 has a display and the communication is in real time, external device 116 can be used to display the current status of injection device 20 as determined by status sensing system 28. Alternatively or additionally, status sensing system 28 may include the display 118 coupled to the module housing 104 that is in communication with controller 96 for communicating the current status of injection device 20.

The illustrated embodiment uses an internal power source in the form of a battery 120 operatively coupled to the controller 96. The power source may include rechargeable batteries, single use batteries, or replaceable batteries. An actuator 122 operatively coupled to the controller 96 and controller 96 includes control logic operative to power on the status sensing system 28 from a low power state. Actuator 122 may take the form of a simple on-off switch disposed on the module housing 104 or it may be a sensor which automatically detects contact with the skin of a user, such as a presence switch, and powers the system when contact is sensed. Actuator 122 may take the form of a motion switch or sensor that once the module is moved for a period of time the switch or sensor triggers a signal to the controller to allow power on. The use of such a skin sensor would allow status sensing system 28 to automatically turn on when injection device 20 is handled. It would also, or, alternatively, confirm that injection device 20 is being handled by a user when an injection event occurs. A skin sensor may be associated with the base of the device 20 that will be in contact with the user's skin in preparation for an injection. Controller 96 includes control logic operative to power on the system 28 in responsive to a signal generated by the skin sensor when contact is made.

Status sensing system 28 may also include a temperature sensor 124. The medication within injection device 20 may need to be maintained within a particular temperature range to prevent degradation of the medication. The use of a temperature sensor 124 on status sensing system 28 could be used to help ensure and verify that the injection device 20 has been stored within the proper temperature range. Controller 96 includes control logic operative to display temperature information via the display 118 in response to a signal generated by the temperature sensor 124 and such signal compared to information stored in the memory 112. Temperature information may include messages of "Temp. Ready" or "Temp. Not Ready" or "Warm" or "Cool" or the like.

The operation of status sensing system 28 will now be explained with reference to FIGS. 12-17. In FIG. 12, injection device 20 is in its original configuration where the syringe assembly 22 is in its storage position, piston 32 is in its initial piston position (and syringe barrel 30 holds a full dose of medication), needle guard 42 is still on needle 34 and end cap 36 is mounted on injection device housing 38 and covers proximal opening 40. In this position, a proximal portion of needle hub 35 and needle guard 42 are at least partially disposed within detection zone 100. End cap 36 may also partially extend into detection zone 100. This is the initial storage configuration of the injection device 20 prior to use of injection device 20. The configuration represented by FIG. 12 is referred to herein as the "needle guard present state".

FIG. 13 illustrates injection device 20 after end cap 36 and needle guard 42 have been removed in preparation for an injection event. The syringe assembly 22 is still in its storage position and piston 32 is still in its initial piston position. In this configuration, a small proximal portion of needle hub 35 is disposed in detection zone 100 but needle guard 42 and end cap 36 are not within or even located near detection zone 100. In this condition, injection device 20 is ready to be used in an injection event and is referred to herein as the "injection ready state".

FIG. 14 illustrates injection device 20 during an injection event after syringe assembly 22 has been advanced to its injection position to insert needle 34 into a patient and before the delivery of the medication has been completed. In this configuration, with syringe assembly 22 is in its injection position, a distal portion of needle hub 35 and a proximal portion of syringe barrel 30 is located within detection zone 100. Piston 32 has not yet reached its final piston position in this configuration and may either be in its initial piston position or have partially traveled toward its final piston position. Piston 32 is not located within the detection zone 100 in this configuration. The configuration represented by FIG. 14 is referred to herein as the "needle insertion state".

FIG. 15 illustrates injection device 20 at that point in the injection process when the delivery of medication has been completed and piston 32 has reached its final piston position. In this configuration, syringe assembly 22 is in its injection position with a distal portion of needle hub 35 and a proximal portion of syringe barrel 30 in the detection zone 100. At least a portion of piston 32, which is located in its final piston position, is also in the detection zone 100. The configuration of FIG. 15 is referred to herein as the "drug delivered state."

FIG. 16 illustrates injection device 20 after the injection has been completed and syringe assembly 22 has been retracted into a storage position with needle 34 disposed within injection device housing 38. It is noted that, as used herein, syringe assembly 22 is considered to be in a storage position when needle 34 is disposed within injection device housing 38 and does not project outwardly therefrom. The initial storage positon of syringe assembly 22 (in FIG. 12) does not necessarily correspond exactly to the storage position of syringe assembly 22 after it has been retracted following an injection event (in FIG. 16). In the illustrated embodiment, the storage position of syringe assembly 22 in FIG. 16 differs slightly from that of FIG. 12 with the syringe assembly 22 being retracted slightly more distal into injection device housing 38 in FIG. 16. In the configuration of FIG. 16, needle hub 35 is entirely, or almost entirely, removed from detection zone 100 with only needle 34 extending through detection zone 100. In FIG. 16, piston 32 remains in the final piston position with syringe assembly 22 in its storage position. The configuration represented by FIG. 16 is referred to herein as the "needle retraction state".

As can be understood with reference to the discussion above and FIGS. 12-16, in the illustrated embodiment, needle hub 35 is disposed within detection zone 100 when syringe assembly 22 is in the injection position and needle hub 35 is disposed outside detection zone 100 when syringe assembly 22 is in the storage position. It is also noted that when syringe assembly 22 is in the storage position, piston 32 is disposed outside detection zone 100, and, when syringe assembly 22 is in the injection position, piston 32 is disposed outside detection zone 100 when piston 32 is in the initial piston position and piston 32 is disposed within detection zone 100 when piston 32 is in the final piston position.

In a successful injection event, the stages depicted in FIGS. 12-16 occur in the predefined sequential order depicted by FIGS. 12, 13, 14, 15 and then 16. FIG. 17 illustrates an example of a signal 200 generated by light detector 94 through the different stages of an injection event. During the different stages the signal 200 changes corresponding to the degrees of light detected by the light detector along the different stages. Segment 212 of signal 200 represents the time during which injection device 20 is in the needle guard present state, e.g., the configuration of FIG. 12. Segment 213 of signal 200 represents the time during which injection device 20 is in the injection ready state, e.g., the configuration of FIG. 13. Segment 214 represents the time during which injection device 20 is in the needle insertion state, e.g., the configuration of FIG. 14. Segment 215 represents the time during which injection device 20 is in the drug delivered state, e.g., the configuration of FIG. 15.

Segment 216 represents the time during which injection device 20 is in the needle retraction state, e.g., the configuration of FIG. 16.

As can be seen in FIG. 17, the different status states represented by FIGS. 12-16 generate signals having different values. In the illustrated embodiment, light detector 94 is positioned to detect light reflected by objects in detection zone 100. As a result, a higher signal value is generated when the objects within detection zone 100 reflect more light. The signal values corresponding to these different status states can be stored in the memory of controller 96. Controller 96 is then able to determine the status of injection device 20 by evaluating the signal generated by light detector 94 and determining which of the status states has the nearest value.

To facilitate the evaluation of the light detector signal 200, the different components of the injection device 20 which move into and out of detection zone 100 could be given different surface treatments so that the signal values for each of the different status states are sufficiently different to allow light detector 94 to distinguish between the different states. For example, needle guard 42 could be provided with a more highly reflective surface so that the signal generated during the needle guard present state would be significantly higher than the signal generated during any of the other status states. Alternatively or additionally, other objects might receive surface treatments to reduce their reflective properties to enhance the difference between the amount of light reflected during each of the different status states.

Another method that can be employed by controller 96 to determine the current status state of injection device 20 takes advantage of the predefined sequential order of the status states. In the illustrated embodiment, injection device 20 progresses through the following five status states in the following sequential order: a) the needle guard present state; b) the injection ready state; c) the needle insertion state; d) the drug delivered state; and e) the needle retraction state. Controller 96 can thereby distinguish between two different status states which generate a signal having the same strength so long as those two status states are separated by at least one other status state. For example, controller 96 will start with the initial status state and then move to the next status state when the signal level changes to approximate the next status state and so on until the process is complete.

Where the controller 96 relies on a predetermined sequence of status states, it is possible to use predefined signal strengths to match current signal with status state. If this approach is used, the controller could display an error message if the signal indicates that a status state has occurred out of its proper sequential order.

Alternatively, whether the signal goes up or down as it transitions from one status state to the next could be recorded in the controller's memory 112. In this configuration, the controller 96 can start at the initial status state and then move to the next status state when the signal strength moved in the proper direction. For example, in the illustrated embodiment, the transition from segment 213 to segment 214 involves a rise in signal strength, as a result, when the controller 96 is in injection ready state (segment 213), it would stay in this status state until the signal strength increased at which point the controller would indicate that the status had changed to the needle insertion state (segment 214). This approach could also require that the signal rise or fall by a predefined amount to move from a particular status state to the next sequential status state. In other words, the controller would be looking for a predefined change in signal strength rather than a predefined value for the signal strength.

Although the illustrated embodiment recognizes five different status states, alternative embodiments may recognize more or fewer status states. For example, a status sensing system that identified only the three following status states would still provide significant advantages to users of injection device 20: i) an injection ready state where the syringe assembly is in the storage position and the piston is in the initial piston position; ii) a needle insertion state where the syringe assembly is in the injection position and the piston is in the initial piston position; and iii) a drug delivered state where the syringe assembly is in the injection position and the piston is in the final piston position.

Such a system could also include a fourth status state following the drug delivered state where that fourth status state is a needle retraction state where the syringe assembly is in the storage position and the plunger is in the final piston position Alternatively, the system could include a fourth status state occurring before the injection ready state where that state is a needle guard present state where the syringe assembly is in the storage condition and the needle guard is present. Various other additional status states and combinations of status states may also be employed.

FIGS. 8-10 and 19-22 illustrate the module housing 104. As can be seen in FIG. 8 module housing 104 includes a longitudinal body 125 and a pair of arms 126 extending from the body 125. Arms 126 may extend from an intermediate section of the body 125 so that the body 125 extends farther down proximally relative to the intersection of the arms 126 to define a tail section 125B below the intersection. The arms 126 together with the body 125 define generally a circular opening 128 through which the device is inserted. Arms 126 are configured to grip the exterior of injection device housing 38 to secure module housing 104 to injection device housing 38 and place the interior surface 127 of the body 125 in close if not contacting relationship with the housing 38. The distance that separate the separated arms 126 is sized to allow for passage of outwardly projection buttons or similar control features on injection device housing 38 as module housing 104 is slid into place. Sensor module housing 104 can be mounted on the injection device housing 38 by sliding the distal end 130 of injection device housing 38 through the opening 128 of module housing 104. Alternatively, arms 126 may be formed out of a resiliently flexible material and module housing 104 could be pressed onto injection device housing 38 in a direction transverse to axis 48 that forces arms 126 outwardly as module housing 104 is engaged with injection device housing 38.

In one example, the module housing 104 is coupled to the device housing 38 such that the sensor opening 108 is located below or proximal to the needle hub 35, as shown in FIG. 12. In another example, the module housing 104 is coupled to the device housing 38 such that the sensor opening 108 is located along at least one aspect of the needle 34 and/or needle hub 35. In another example, the module housing 104 is coupled to the device housing 38 such that the sensor opening 108 is located along in close proximity to the transition 115, shown as directly distal to the transition 115 and below the needle hub 35. In another example, the sensor opening 108 is axially disposed proximal to the axial position of the needle hub 35 when the syringe assembly is in the storage position. In one embodiment, cylindrical segment 111 of device housing 38 that includes window portion 110 is directly distal and contacting the base 113 of the device housing 38. At any of these attachment locations about the proximal end opening 40 of the device 20 and near the base 113 and close proximity to the needle hub 35, the module housing 104 is in a position along the device to use a single sensor system to capture the different operational states as described herein. The module housing 104 may allow for reuse on another device. The module configuration may allow minimal if not any changes to the internal mechanisms of the device housing. It may be advantageous to provide a single sensing system positioned at a single attachment location along the device to capture three, four or five of the states: a needle guard present state, an injection ready state, a needle insertion state, a drug delivered state, and a needle retraction state.

In one embodiment, the segment 111 that includes window portion 110 is located along the transition 115 to the base 113. The base 113 is shown enlarged relative to the general size of both of the segment 111 and the remainder of the device housing 38. The module housing 104 is sized and shaped to accommodate such transition in size and shape. The module housing 104 includes a distal portion 104A which includes the arms 126. The distal segment of the opening 128 along the distal portion 104A includes a first cross-sectional area sized to accommodate the general cylindrical cross-sectional area of the segment 111. The proximal segment of the opening 128 along the proximal portion 104B that corresponds to the tail section 125B of the body 125 includes a second cross-sectional area, larger than the first cross-sectional area of the distal segment of the opening 128, sized to accommodate the enlarged cross-sectional area of the base 113 where the base proximally flares out from the cylindrical segment. Such change in size permits the base 113 to function as a physical stop when sliding the module housing 104 in the proximal direction to enhance the axial alignment of the sensor opening 108 relative to components to be sensed as shown in FIGS. 12-16. In one example, the distal portion 104A of the body that includes the distal segment of the opening 128 formed by the arms 126 defines a cylindrical configuration to accommodate the cylindrical segment 111, and the proximal tail segment 125B of the body 125 is sized to accommodate a proximally flaring configuration of the base 113, as shown in FIG. 12. In one example, the cross-sectional area of the distal portion 104A of opening 128 is sized smaller than the cross-sectional area of the enlarged base 125 such that the module bottoms out when engaging the base.

FIGS. 19-22 illustrate the user interface of status sensor system module 28. Display 118 includes one or more indicators. For example, display 118 includes a first indicator 132, shown as a wireless communication icon, which indicates when system module 28 is wirelessly linked with an external device. The display 118 includes a second indicator 134, shown as a battery icon, to inform the user of the charge level of battery 120. Display 118 includes a third indicator 136, shown as an alphanumeric text, to inform the user of the status of injection device 20. Display may include at least one of the first, second, third indicators 132, 134, 136 or any combination thereof. Display can include LEDs, graphical icons and/or alphanumerical characters, or any combination thereof, for messaging to the user.

Figure 19:
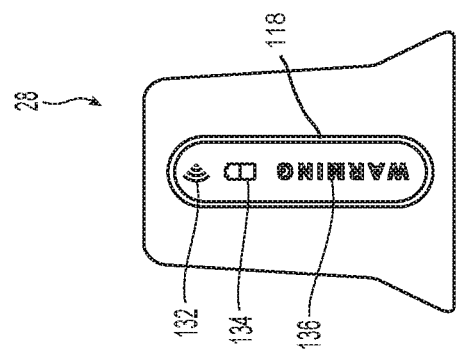
FIG. 19 is a front view of the status sensing system module with a display indicating a message.

In FIG. 19, display 118 displays the status message "WARMING". This message is displayed when status sensor system 28 is initially activated and controller 96 is being initialized. After system 28 is actuated and ready for operation it will begin displaying messages indicating the status state of injection device 20 as determined by controller 96 based at least in part on the signal 200 generated by light detector 94.

Figure 22:
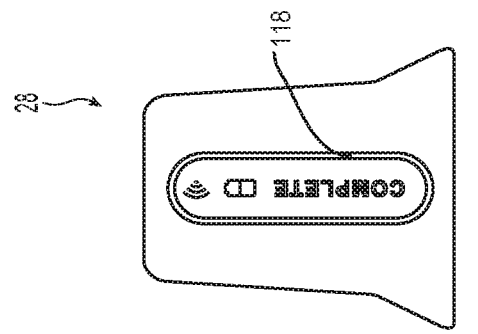
FIG. 22 is a front view of the status sensing system module with a display indicating another message.
Figure 21:
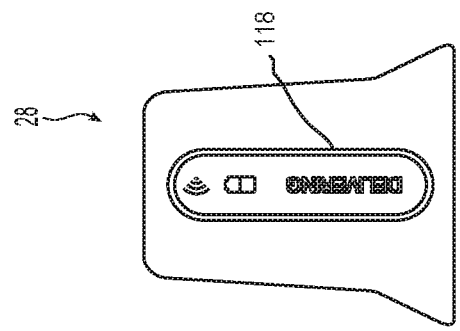
FIG. 21 is a front view of the status sensing system module with a display indicating another message.
Figure 20:
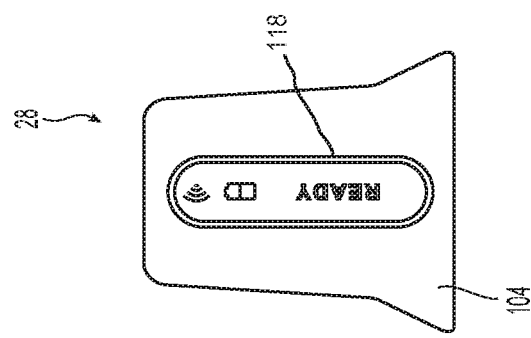
FIG. 20 is a front view of the status sensing system module with a display indicating another message.

In FIG. 20, the displayed status message is "READY" which corresponds to the injection ready state described above and represented by FIG. 13. In FIG. 21, the displayed message is "DELIVERING" which corresponds to the needle insertion state described above and represented by FIG. 14. In FIG. 22, the displayed message is "COMPLETE" which corresponds to the drug delivered state described above and represented by FIG. 15.

Figure 23:
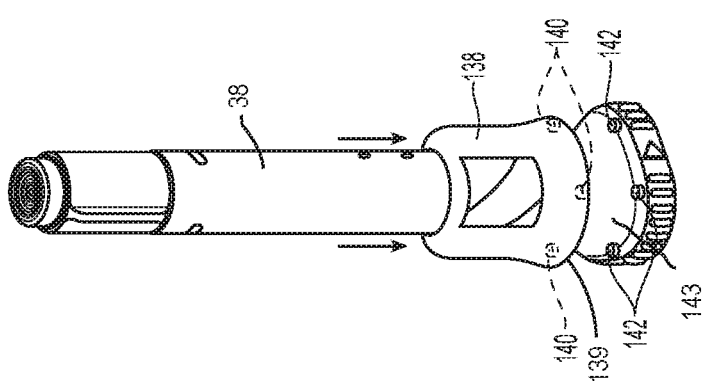
FIG. 23 is a perspective view of the injection device with an alternative embodiment of a status sensing system module employing magnets in its mounting to the injection device.

FIGS. 23-28 illustrate alternative sensor module housings, which include, although not shown, at least some of the sensor system components in FIG. 18 for an operational module. FIG. 23 illustrates a sensor module housing 138 that can be slid onto the injection device housing. Module housing 138 can be properly aligned and maintained in its proper position on the injection device housing using a magnetic coupling. In one example, one or more magnets 140 are coupled to module housing 138 for magnetic coupling with corresponding magnets 142 coupled to the injection device housing to secure and align the two housings. In one example, the magnets 140 are disposed along the proximal end 139 of the module housing 138, and the magnets 140 may be embedded into the material of the module housing 138 or may be housed within the module housing 138. In one example, the magnets 142 are disposed along a distal surface of the base 143 of the injection device housing 38, and the magnets 142 may be embedded into the material of the device housing 38 or may be housed within the module housing 38. In one example, the magnets 140 are disposed along the proximal facing surface of the module housing 138, and the magnets 142 are disposed along the distal facing surface of the enlarged base 143 of the injection device housing 38. Various alternative embodiments could substitute one of the sets of magnets for a ferrous material that is attracted to the magnets on the other housing.

Figure 24:
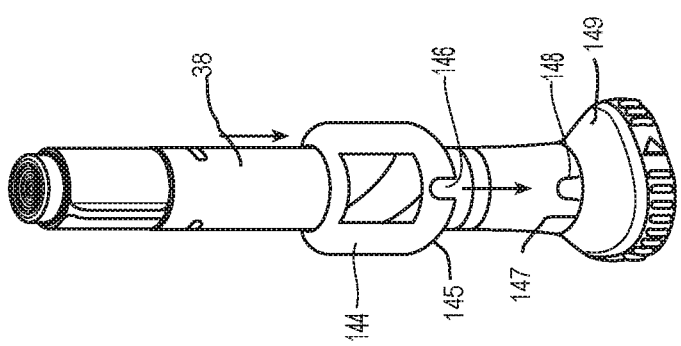
FIG. 24 is a perspective view of the injection device with another embodiment of a status sensing system module having an alternative mounting structure.

FIG. 24 illustrates a sensor module housing 144 that can be slid onto the injection device housing and includes a notch 146 that can be sized and shaped to receive a correspondingly shaped projection 148 located on the sensor device housing 38. In one example, the notch 146 is an axial slot defined by the proximal end 145 of the module housing 144. In one example, the projection 148 is an axial extending projection that is coupled to or otherwise molded with device housing 38 along the transition 147 from the device housing's general cross-sectional size and shape to the enlarged base 149 that has a different shape and larger size than the general size and shape of the device housing. Engagement between notch 146 and projection 148 properly positions module housing 144 on the injection device housing 38. Notch 146 and projection 148 may also be configured such that engagement of notch 146 with projection 148 secures module housing 144 on the injection device housing in addition to properly aligning it. It is further noted that various other interfitting projections and recesses may be used to properly align and/or secure the two housings together.

Figure 25:
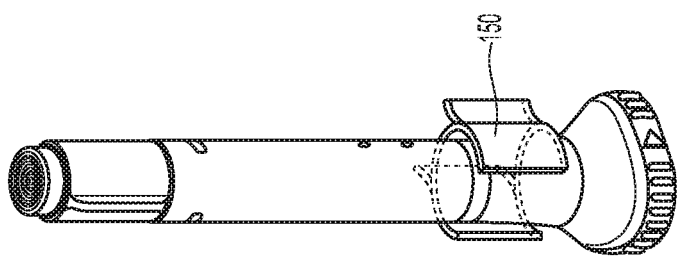
FIG. 25 is a perspective view of the injection device with another embodiment of a status sensing system module having an alternative mounting structure.
Figure 26:
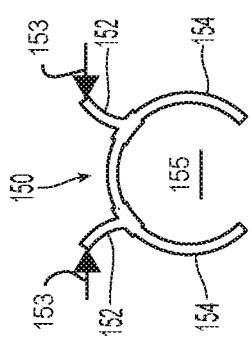
FIG. 26 is a top view of the status sensing system module of FIG. 25.

FIGS. 25-26 illustrate a sensor module housing 150 having a hinge mechanism 152 that allows opposed arms 154 to pivot outwardly away from their natural state shown upon application of a radially inward force in the direction of arrows 153. Pivoting arms 154 outwardly enlarge the cross-sectional area of the slot 155 between the arms 154 to allow module housing 150 to be engaged with the injection device housing in a direction transverse to axis 48. Once sensor module housing 150 is properly engaged and positioned on the injection device housing, the application of force is removed and arms 154 are resilient to pivot inwardly to its natural state shown to firmly engage the injection device housing and thereby secure module housing 150 on the injection device housing.

Figure 27:
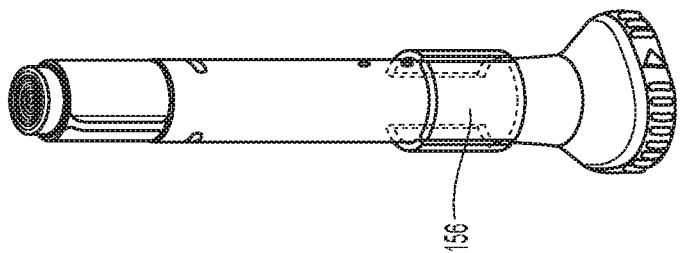
FIG. 27 is a perspective view of the injection device with another embodiment of a status sensing system module having an alternative mounting structure.
Figure 28:
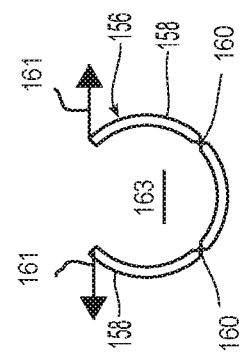
FIG. 28 is a top view of the status sensing system of FIG. 27.

FIGS. 27-28 illustrate a sensor module housing 156 having an opposed pair of arms 158 for engaging the injection device housing. Hinges 160 are formed integral with arms 158 out of a resiliently flexible material that allow arms 158 to be pivoted outwardly from its natural state upon application of a radially outward force in the direction of arrows 161 to allow module housing 156 to be mounted on the injection device housing. Pivoting arms 158 outwardly enlarge the cross-sectional area of the slot 163 between the arms 158 to allow module housing 156 to be engaged with the injection device housing in a direction transverse to axis 48. Once module housing 156 is properly engaged and positioned on the injection device housing, the application of force is removed and arms 158 are resilient to pivot inwardly to its natural state shown to firmly engage the injection device housing and thereby secure module housing 156 on the injection device housing.

Various other structures and methods can also be employed for securing and/or aligning a sensor module housing on the injection device housing.

While this invention has been described as having an exemplary design, the embodiments of the present disclosure may be further modified within the spirit and scope of this disclosure. This application is therefore intended to cover any variations, uses, or adaptations of the disclosed embodiments using its general principles.

Various aspects are described in this disclosure, which include, but are not limited to, the following aspects:

1. An injection device assembly comprising: a device housing defining an interior volume extending about a longitudinal axis, a proximal opening in communication with the interior volume; a syringe assembly at least partially disposed within the interior volume, the syringe assembly including a barrel, and a piston disposed within the barrel, wherein the syringe assembly is moveable relative to the device housing along the longitudinal axis between a storage position where an injection needle extendable from the barrel is concealed within the injection device housing and an injection position where the injection needle projects proximally beyond the proximal opening, wherein the piston is movable between an initial piston distal position within the barrel and a final piston proximal position; a drive mechanism coupled with the syringe assembly and including a plunger engageable with the piston, wherein relative movement between the syringe assembly the device housing moves the syringe assembly between the storage position and the injection position in response to proximal advancement of the drive mechanism, wherein, during advancement of the drive mechanism proximally, the piston advances from the initial piston distal position to the final piston proximal position; a status sensing system including a light emitter configured to emit electromagnetic radiation in a direction transverse to the longitudinal axis and into the interior volume, a light detector configured to detect electromagnetic radiation emitted from the light emitter and configured to generate a signal responsive to the detected electromagnetic radiation, and a controller in electrical communication with the light emitter and the light detector, the controller configured to determine an operational status of the device based at least in part upon the generated signal, wherein the controller is configured to determine a current status condition between at least three status conditions of the device including: i) an injection ready state wherein the syringe assembly is in the storage position and the piston is in the initial piston distal position; ii) a needle insertion state wherein the syringe assembly is in the injection position and the piston is in the initial piston distal position; and iii) a drug delivered state wherein the syringe assembly is in the injection position and the piston is in the final piston proximal position 2. The injection device assembly of any one of aspects 1, 3-19 wherein the status states occur in a predefined order with the injection ready state occurring before the needle insertion state and the drug delivered state occurring after the needle insertion state.

3. The injection device assembly of any one of aspects 1-2, and 4-19 wherein the controller is configured to determine the current status condition from at least four status conditions, wherein the status conditions includes (iv) a needle retraction state wherein the syringe assembly is in the storage position and the plunger is in the final piston distal position.

4. The injection device assembly of any one of aspects 1-3, and 5-19 further including a needle guard removably attachable to the syringe assembly, wherein the controller is configured to determine the current status condition from at least four status conditions, wherein the status conditions includes (iv) a needle guard present state wherein the syringe assembly is in the storage condition, the needle guard is attached to the syringe assembly, and the piston is in the initial piston distal position.

5. The injection device assembly of any one of aspects 1-4 and 6-19 further including a sensor module housing including the status sensing system, wherein the sensor module housing is removably attachable to the injection device housing.

6. The injection device assembly of aspect 5 wherein the device housing defines a window portion configured to allow a transmission of electromagnetic radiation emitted by the light emitter into the interior volume, and allow a transmission of electromagnetic radiation from the interior volume to the light detector when the sensor module housing is attached to the injection device housing.

7. The injection device assembly of aspect 5 wherein the sensor module housing includes an interior space, wherein the light emitter, the light detector, and the controller are disposed within the interior space, the sensor module housing further including a sensor opening in communication with the interior space, wherein the light emitter is positioned to emit electromagnetic radiation outwardly through the sensor opening and the light detector is positioned to detect electromagnetic radiation entering the interior space through the sensor opening.

8. The injection device assembly of aspect 7 wherein the device housing defines a window portion that is in communication with the sensor opening when the sensor module housing is attached to the device housing, wherein the window portion allows a transmission of electromagnetic radiation emitted by the light emitter into the interior volume and allows a transmission of electromagnetic radiation from the interior volume to the light detector.

9. The injection device assembly of aspect 8 wherein the window portion of the injection device housing is defined by a transparent polymeric material.

10. The injection device assembly of any one of aspects 1-9 and 11-19 further including a needle guard removably attachable to the syringe assembly, wherein the controller is configured to determine the current status condition from at least five status conditions, the status conditions further including: iv) a needle guard present state wherein the syringe assembly is in the storage condition, the needle guard is attached to the syringe assembly and the piston is in the initial piston distal position; and v) a needle retraction state wherein the syringe assembly is in the storage position and the plunger is in the final piston proximal position.

11. The injection device assembly of aspect 10 wherein the status states occur in a predefined order with the status states occurring in the following order: a) the needle guard present state; b) the injection ready state; c) the needle insertion state; d) the drug delivered state; and e) the needle retraction state.

12. The injection device assembly of any one of aspects 1-11 and 13-19 wherein the device housing defines a detection zone within the interior volume and proximate the proximal opening, wherein the light emitter is positioned to emit electromagnetic radiation into the detection zone and the light detector is positioned to detect electromagnetic radiation from the detection zone.

13. The injection device assembly of aspect 12 wherein a substantial portion of the needle hub is disposed within the detection zone when the syringe assembly is in the injection position, and a substantial portion of the needle hub is disposed outside the detection zone when the syringe assembly is in the storage position.

14. The injection device assembly of aspect 5, wherein the sensor module housing further including a sensor opening, wherein the light emitter is positioned to emit electromagnetic radiation outwardly through the sensor opening and the light detector is positioned to detect electromagnetic radiation entering through the sensor opening, wherein the sensor opening of the sensor module housing is axially disposed proximal to an axial position of the needle hub when the syringe assembly is in the storage position.

15. The injection device assembly of aspect 14, wherein the sensor module housing includes a body and a pair of gripping arms extending from the body, the body and the gripping arms defining an opening through which the device is inserted, wherein a distal segment of the opening is sized to accommodate a cylindrical segment of the device housing, and the distal segment of the opening sized smaller than a base of the device housing that is sized larger than the cylindrical segment.

16. The injection device assembly of aspect 14, wherein the sensor module housing includes axially placed magnets to couple to corresponding magnets of the device housing.

17. The injection device assembly of aspect 14, wherein the sensor module housing includes one of a slot or a projection, and the device housing includes the other of the slot or a projection sized and shaped to couple to the one of the slot or the projection of the sensor module housing.

18. The injection device assembly of aspect 14, wherein the sensor module housing includes a body and a pair of gripping arms extending from the body, wherein the gripping arms are capable of pivoting out in order to transversely attach to the device housing.

19. The injection device assembly of any one of aspects 1-18, including a medication disposed within the barrel.

20. A method of determining a current status condition of an injection device, the injection device including a device housing defining an interior volume extending about a longitudinal axis, a syringe assembly at least partially disposed within the interior volume, the syringe assembly including a barrel, a piston disposed within the barrel, and a needle assembly including a needle hub and an injection needle, wherein the syringe assembly is moveable relative to the device housing between a storage position where the injection needle is disposed within the injection device housing and an injection position where the injection needle projects proximally beyond a proximal opening of the device housing, wherein the piston is movable between an initial piston distal position within the barrel and a final piston proximal position, and a status sensing system including a light emitter configured to emit electromagnetic radiation in a direction transverse to the longitudinal axis and into the interior volume, a light detector configured to detect electromagnetic radiation emitted from the light emitter and configured to generate a signal responsive to the detected electromagnetic radiation, the method including: determining an injection ready state wherein the syringe assembly is in the storage position and the piston is in the initial piston distal position; determining a needle insertion state wherein the syringe assembly is in the injection position and the piston is in the initial piston distal position; and determining a drug delivered state wherein the syringe assembly is in the injection position and the piston is in the final piston proximal position.

21. The method of aspect 20, wherein the injection device includes a needle guard removably attachable to the syringe assembly, the method further including: determining a needle guard present state wherein the syringe assembly is in the storage condition, the needle guard is attached to the syringe assembly, and the piston is in the initial piston distal position; or determining a needle retraction state wherein the syringe assembly is in the storage position and the plunger is in the final piston proximal position.

22. A sensor module for removable attachment to an injection device, including: a sensor module housing wherein the sensor module housing includes a body defining an interior and a pair of gripping arms extending from the body, the gripping arms separated from one another by a slot to receive the injection device, wherein a distal segment of the slot formed by the gripping arms includes a cylindrical configuration, and a proximal tail segment of the body is sized to accommodate a proximally flaring configuration; and a status sensing system coupled to the sensor module housing and including a light emitter configured to emit electromagnetic radiation in a direction transverse to a longitudinal axis of the injection device, a light detector configured to detect electromagnetic radiation emitted from the light emitter and configured to generate a signal responsive to the detected electromagnetic radiation, and a controller in electrical communication with the light emitter and the light detector, the controller configured to determine a current status of the injection device based at least in part upon the generated signal.

23. The sensor module of aspect 22, further including a display operatively coupled to the controller.

24. The sensor module of any one of aspects 22-23, further including a wireless transmission communication module operatively to the controller.

What is claimed is:
1. An injection device assembly comprising:
a device housing defining an interior volume extending about a longitudinal axis, a proximal opening in communication with the interior volume;
a syringe assembly at least partially disposed within the interior volume, the syringe assembly including a barrel, and a piston disposed within the barrel, wherein the syringe assembly is moveable relative to the device housing along the longitudinal axis between a storage position where an injection needle extendable from the barrel is concealed within the device housing and an injection position where the injection needle projects proximally beyond the proximal opening, wherein the piston is movable between an initial piston distal position within the barrel and a final piston proximal position;
a drive mechanism coupled with the syringe assembly and including a plunger engageable with the piston, wherein relative movement between the syringe assembly and the device housing moves the syringe assembly between the storage position and the injection position in response to proximal advancement of the drive mechanism, wherein, during advancement of the drive mechanism proximally, the piston advances from the initial piston distal position to the final piston proximal position;
a status sensing system including a light emitter configured to emit electromagnetic radiation in a direction transverse to the longitudinal axis and into the interior volume, a light detector configured to detect electromagnetic radiation emitted from the light emitter and configured to generate a signal responsive to the detected electromagnetic radiation, and a controller in electrical communication with the light emitter and the light detector, the controller configured to determine, based at least in part upon the generated signal, a current status condition between at least three status conditions of said injection device assembly including:
i) an injection ready state wherein the syringe assembly is in the storage position and the piston is in the initial piston distal position;
ii) a needle insertion state wherein the syringe assembly is in the injection position and the piston is in the initial piston distal position; and
iii) a drug delivered state wherein the syringe assembly is in the injection position and the piston is in the final piston proximal position.

2. The injection device assembly of claim 1, wherein the status conditions occur in a predefined order with the injection ready state occurring before the needle insertion state and the drug delivered state occurring after the needle insertion state.

3. The injection device assembly of claim 1, wherein the controller is configured to determine said current status condition from at least four status conditions, wherein the status conditions includes (iv) a needle retraction state wherein the syringe assembly is in the storage position and the piston is in the final piston proximal position.

4. The injection device assembly of claim 1 further comprising a needle guard removably attachable to the syringe assembly, wherein the controller is configured to determine said current status condition from at least four status conditions, wherein the status conditions includes (iv) a needle guard present state wherein the syringe assembly is in the storage position, the needle guard is attached to the syringe assembly, and the piston is in the initial piston distal position.

5. The injection device assembly of claim 1 further comprising a sensor module housing including the status sensing system, wherein the sensor module housing is removably attachable to the device housing.

6. The injection device assembly of claim 5, wherein the device housing defines a window portion configured to allow transmission of electromagnetic radiation emitted by the light emitter into the interior volume, and allow transmission of electromagnetic radiation from the interior volume to the light detector when the sensor module housing is attached to the device housing.

7. The injection device assembly of claim 5, wherein the sensor module housing includes an interior space, wherein the light emitter, the light detector, and the controller are disposed within the interior space, the sensor module housing further comprising a sensor opening in communication with the interior space, wherein the light emitter is positioned to emit electromagnetic radiation outwardly through the sensor opening and the light detector is positioned to detect electromagnetic radiation entering the interior space through the sensor opening.

8. The injection device assembly of claim 7, wherein the device housing defines a window portion that is in communication with the sensor opening when the sensor module housing is attached to the device housing, wherein the window portion allows transmission of electromagnetic radiation emitted by the light emitter into the interior volume and allows transmission of electromagnetic radiation from the interior volume to the light detector.

9. The injection device assembly of claim 8, wherein the window portion of the device housing is defined by a transparent polymeric material.

10. The injection device assembly of claim 1 further comprising a needle guard removably attachable to the syringe assembly, wherein the controller is configured to determine said current status condition from at least five status conditions, the status conditions further including:
iv) a needle guard present state wherein the syringe assembly is in the storage position, the needle guard is attached to the syringe assembly and the piston is in the initial piston distal position; and
v) a needle retraction state wherein the syringe assembly is in the storage position and the piston is in the final piston proximal position.

11. The injection device assembly of claim 10 wherein the status conditions occur in a predefined order with the status conditions occurring in the following order:
a) the needle guard present state;
b) the injection ready state;
c) the needle insertion state;
d) the drug delivered state; and
e) the needle retraction state.

12. The injection device assembly of claim 1, wherein the device housing defines a detection zone within the interior volume and proximate the proximal opening, wherein the light emitter is positioned to emit electromagnetic radiation into the detection zone and the light detector is positioned to detect electromagnetic radiation from the detection zone.

13. The injection device assembly of claim 12, wherein a substantial portion of a needle hub is disposed within the detection zone when the syringe assembly is in the injection position, and the substantial portion of the needle hub is disposed outside the detection zone when the syringe assembly is in the storage position.

14. The injection device assembly of claim 13, wherein the injection device assembly further comprises a sensor module housing including the status sensing system, wherein the sensor module housing is removably attachable to the device housing, and wherein the sensor module housing further comprises a sensor opening, wherein the light emitter is positioned to emit electromagnetic radiation outwardly through the sensor opening and the light detector is positioned to detect electromagnetic radiation entering through the sensor opening, wherein the sensor opening of the sensor module housing is axially disposed proximal to an axial position of the needle hub when the syringe assembly is in the storage position.

15. The injection device assembly of claim 14, wherein the sensor module housing includes a body and a pair of gripping arms extending from the body, the body and the gripping arms defining an opening through which the device housing is inserted, wherein a distal segment of the opening is sized to accommodate a cylindrical segment of the device housing, and the distal segment of the opening is sized smaller than a base of the device housing that is sized larger than the cylindrical segment.

16. The injection device assembly of claim 14, wherein the sensor module housing includes axially placed magnets to couple to corresponding magnets of the device housing.

17. The injection device assembly of claim 14, wherein the sensor module housing includes one of a slot or a projection, and the device housing includes the other of the slot or the projection sized and shaped to couple to the one of the slot or the projection of the sensor module housing.

18. The injection device assembly of claim 14, wherein the sensor module housing includes a body and a pair of gripping arms extending from the body, wherein the gripping arms are capable of pivoting out in order to transversely attach to the device housing.

19. The injection device assembly of claim 1, including a medication disposed within the barrel.

20. A method of determining a current status condition of an injection device, the injection device including a device housing defining an interior volume extending about a longitudinal axis, a syringe assembly at least partially disposed within the interior volume, the syringe assembly including a barrel, and a piston disposed within the barrel, wherein the syringe assembly is moveable relative to the device housing between a storage position where an injection needle of the syringe assembly is disposed within the device housing and an injection position where the injection needle projects proximally beyond a proximal opening of the device housing, wherein the piston is movable between an initial piston distal position within the barrel and a final piston proximal position, and a status sensing system including a light emitter configured to emit electromagnetic radiation in a direction transverse to the longitudinal axis and into the interior volume, a light detector configured to detect electromagnetic radiation emitted from the light emitter and configured to generate a signal responsive to the detected electromagnetic radiation, the method comprising:

determining, based on the generated signal, an injection ready state wherein the syringe assembly is in the storage position and the piston is in the initial piston distal position;

determining, based on the generated signal, a needle insertion state wherein the syringe assembly is in the injection position and the piston is in the initial piston distal position; and determining, based on the generated signal, a drug delivered state wherein the syringe assembly is in the injection position and the piston is in the final piston proximal position.

21. The method of claim 20, wherein the injection device includes a needle guard removably attachable to the syringe assembly, the method further comprising: determining, based on the generated signal, a needle guard present state wherein the syringe assembly is in the storage position, the needle guard is attached to the syringe assembly, and the piston is in the initial piston distal position; or determining, based on the generated signal, a needle retraction state wherein the syringe assembly is in the storage position and the piston is in the final piston proximal position.

* * * * *